US007758577B2

(12) United States Patent
Nobis et al.

(10) Patent No.: US 7,758,577 B2
(45) Date of Patent: Jul. 20, 2010

(54) MONOPOLAR RESECTION DEVICE AND METHOD OF USE

(75) Inventors: Rudolph Nobis, Mason, OH (US); Ifung Lu, Skokie, IL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 376 days.

(21) Appl. No.: 11/567,001

(22) Filed: Dec. 5, 2006

(65) Prior Publication Data

US 2008/0132891 A1 Jun. 5, 2008

(51) Int. Cl.
*A61B 18/14* (2006.01)

(52) U.S. Cl. .......................................... 606/45; 606/52

(58) Field of Classification Search .................. 606/45, 606/51, 52
See application file for complete search history.

(56) References Cited

U.S. PATENT DOCUMENTS

| | | | | |
|---|---|---|---|---|
| 2,068,721 | A * | 1/1937 | Wappler | 606/46 |
| 5,797,938 | A | 8/1998 | Paraschac et al. | |
| 5,800,449 | A * | 9/1998 | Wales | 606/172 |
| 5,827,279 | A * | 10/1998 | Hughett et al. | 606/45 |
| 6,436,097 | B1 * | 8/2002 | Nardella | 606/45 |
| 6,464,702 | B2 * | 10/2002 | Schulze et al. | 606/51 |
| 6,478,794 | B1 * | 11/2002 | Trapp et al. | 606/45 |
| 6,679,882 | B1 * | 1/2004 | Kornerup | 606/51 |
| 6,773,435 | B2 | 8/2004 | Schulze et al. | |
| 7,226,465 | B1 * | 6/2007 | Farin | 606/205 |
| 7,384,421 | B2 * | 6/2008 | Hushka | 606/51 |
| 7,540,872 | B2 * | 6/2009 | Schechter et al. | 606/50 |
| 2002/0107517 | A1 | 8/2002 | Witt et al. | |
| 2003/0171747 | A1 * | 9/2003 | Kanehira et al. | 606/45 |
| 2003/0191464 | A1 * | 10/2003 | Kidooka | 606/45 |
| 2004/0054365 | A1 * | 3/2004 | Goble | 606/34 |
| 2004/0236326 | A1 | 11/2004 | Schulze et al. | |
| 2005/0261674 | A1 * | 11/2005 | Nobis et al. | 606/45 |
| 2006/0189980 | A1 * | 8/2006 | Johnson et al. | 606/51 |

FOREIGN PATENT DOCUMENTS

| | | |
|---|---|---|
| EP | 1637086 | 3/2006 |

OTHER PUBLICATIONS

International Search Report Mar. 26, 2008, International Searching Authority.

* cited by examiner

*Primary Examiner*—Lee S Cohen

(57) ABSTRACT

Methods and devices are provided for delivering monopolar energy to a treatment area in order to cut and/or coagulate tissue. In one embodiment, the device can include an elongated shaft having a distal end that is mated to a cutting head. The cutting head can include opposed jaws and an active monopolar cutting element coupled to at least one of the jaws and adapted to communicate with an energy source for delivering energy to tissue grasped between the jaws. In an exemplary embodiment, the cutting element is slidably retractable relative to the jaws to cut and/or coagulate tissue engaged therebetween. Exemplary methods for cutting and/or coagulating tissue are also provided.

19 Claims, 8 Drawing Sheets

15 16a 18 17a 34 35 14 16 17b 21 36 16b 20 37 24b

MONOPOLAR RESECTION DEVICE AND METHOD OF USE

FIELD OF THE INVENTION

The invention relates to devices and methods for resecting tissue.

BACKGROUND OF THE INVENTION

Many conventional surgical instruments incorporate cutting blades or the application of energy for transecting and/or cauterizing tissue held within a pair of jaws. A potential difficulty with cutting blades of such instruments is "tissue-tagging" when the blade does not completely cut through all the tissue held in the jaws. This can occur, for example, if the cutting edge of the blade is dull or nicked. Another reason tissue-tagging can occur, or even some bleeding after the tissue is coagulated and cut, is that the tissue is not held firmly enough within the jaws of the instrument as the cutting blade is passed through the tissue held. When tissue is initially clamped within the jaws of the instrument, the clamping force can be very high due to the elasticity of the fluid-containing tissue. But after the tissue has been compressed for a period of time, and then is coagulated, most of the fluid has been driven out of the tissue, with the result that the elasticity of the tissue is greatly reduced. The clamping force on the tissue is also decreased so that the tissue can shift within the jaws as a cutting blade is passed through it. This presents the possibility that not all the tissue will be cut, or the cutting blade will pass through a portion of tissue that is not fully coagulated.

An alternative to using mechanical cutting blades is to use bipolar electrosurgical cutting devices. While such devices offer some advantages over mechanical cutting blades, use of such devices can result in excessive lateral spreading of the thermally affected zone of tissue resulting in damage to healthy tissue, especially if the operator is inexperienced or otherwise not careful.

Accordingly, there is a need for devices and methods for safely, accurately, and efficiently delivering a therapeutically effective amount of monopolar energy to cut and/or coagulate tissue.

SUMMARY OF THE INVENTION

The present invention generally provides methods and devices for cutting and/or coagulating tissue. In one embodiment, a monopolar resection device is provided which includes an elongate shaft having proximal and distal ends, and first and second jaws mated to the distal end of the elongate shaft. The jaws are adapted to engage tissue therebetween and at least one of the jaws can include a monopolar cutting element coupled thereto. The monopolar cutting element can be adapted to couple to an energy source for delivering energy to the cutting element. In an exemplary embodiment, the cutting element is slidably movable between an extended position in which the cutting element is positioned adjacent to a distal end of the jaws, and a retracted position in which the cutting element is positioned adjacent to a proximal end of the jaws. Sliding the cutting element between these positions allows for a large amount of energy to be delivered to a localized treatment area.

While the cutting element can have a variety of configurations, in one exemplary embodiment a portion of the cutting element can be in the form of a rigid needle. The needle can extend substantially transverse, and more preferably substantially perpendicular, to a longitudinal axis of the first and second jaws. In another embodiment, the first jaw can include a first cutting element slidably coupled thereto, and the second jaw can include a second cutting element slidably coupled thereto.

The device can also include other features, such as a handle mated to the proximal end of the elongate shaft. The handle can include an actuator located thereon for moving the jaws between an open position in which the jaws are spaced a distance apart from one another for receiving tissue therebetween, and a closed position in which the jaws are positioned adjacent to one another and adapted to engage tissue therebetween. The device can also include a retraction knob mated to the handle for moving the cutting element from the extended position to the retracted position.

Methods for cutting and/or coagulating tissue are also provided, and in one exemplary embodiment the method can include positioning tissue to be treated between opposed jaws of a tissue grasping device and moving the opposed jaws to a closed position to engage the tissue disposed therebetween. A monopolar energy source can be activated to deliver energy to a cutting element coupled to at least one of the opposed jaws, and the cutting element can be slidably retracted relative to the opposed jaws to cut and/or coagulate the tissue. In one exemplary embodiment, the device can include a flexible elongate shaft that is inserted through a tortuous body lumen to position the opposed jaws located on a distal end of the flexible elongate shaft adjacent to the tissue to be cut and/or coagulated. The device can be delivered, for example, to an abdominal cavity via a natural orifice. The method can also include actuating a trigger formed on a handle of the device to move the jaws from an open position to a closed position in order to grasp tissue positioned therebetween.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Various exemplary methods and devices are provided herein for accurately, efficiently, and safely delivering a therapeutically effective amount of monopolar energy to a treatment area to cut and/or coagulate tissue. In general, a monopolar resection device is provided having a cutting head adapted to be delivered to the treatment area. The cutting head can include a pair of opposed jaws adapted to open and close in order to grasp tissue therebetween, and at least one cutting element mated to at least one of the jaws for cutting tissue grasped between the jaws. The cutting element cab be adapted to couple to an energy source for delivering energy to the cutting element. In an exemplary embodiment, the cutting element is slidably coupled to the jaw to allow the cutting element to slide back and forth through grasped tissue. The device can also include a handle having various features for controlling the jaws and/or cutting element.

Figure 1A:
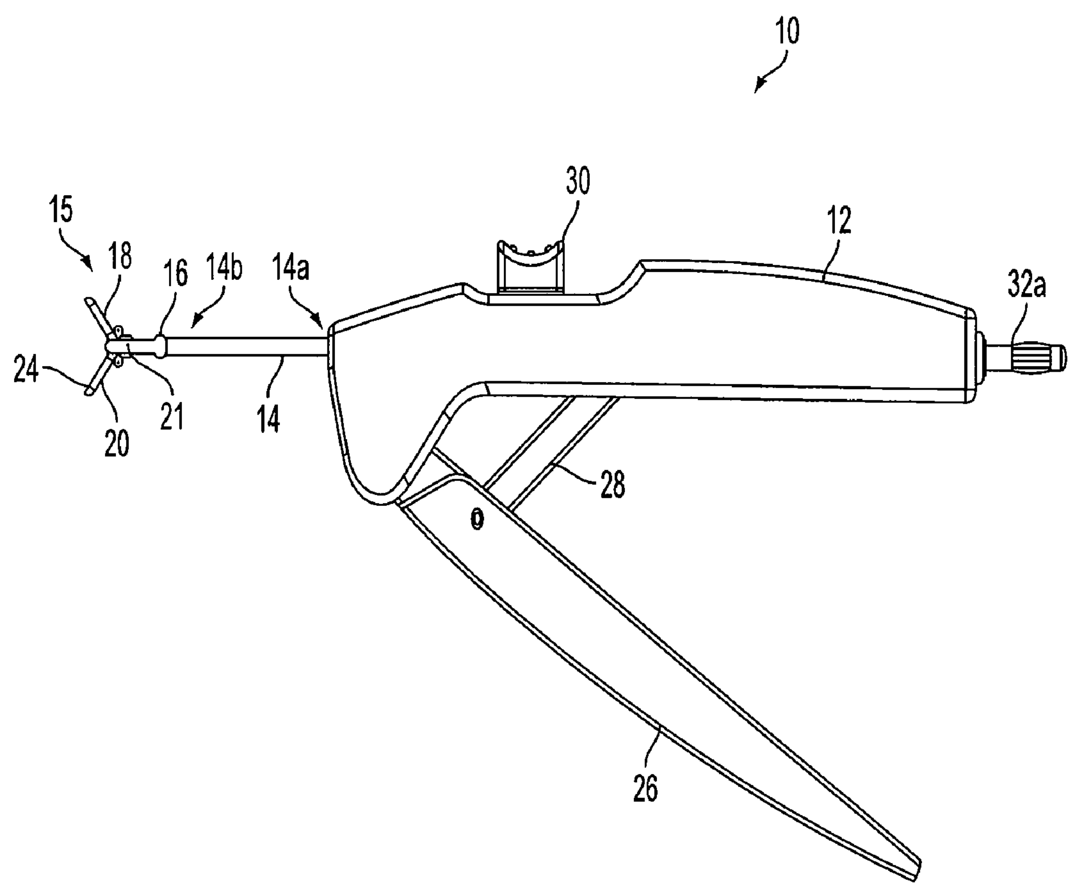
FIG. 1A is a side view of one embodiment of a monopolar resection device.
Figure 1B:
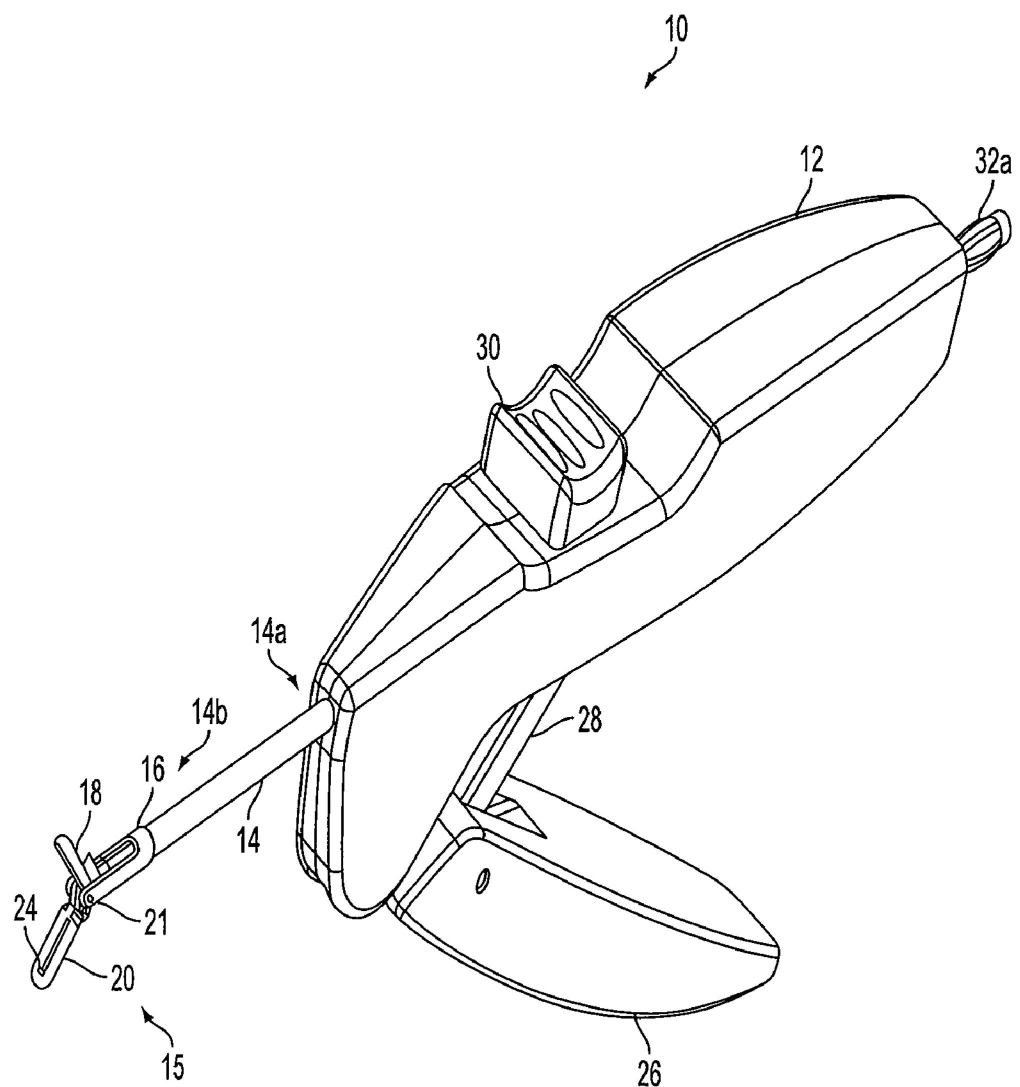
FIG. 1B is a perspective view of the device of FIG. 1A.

FIGS. 1A and 1B show one exemplary embodiment of a monopolar resection device 10. As shown, the device 10 generally includes an elongated shaft 14 adapted for delivery to a desired treatment area. The shaft 14 can be flexible or non-flexible depending on the intended use, but in an exemplary embodiment the shaft 14 is flexible to allow for insertion through a tortuous body lumen, and more preferably to allow the shaft 14 to be passed through a working channel of an endoscope disposed through a body lumen, such as the colon or esophagus. The shaft 14 can have a proximal end 14*a* that is mated to a handle 12 and a distal end 14*b* that is mated to the cutting head 15. As further shown in FIGS. 1A and 1B, the cutting head 15 generally includes opposed jaws 18, 20 that are capable of opening and closing to grasp tissue therebetween. At least one of the jaws, e.g., jaw 20, can include an electrically active cutting element 24 coupled thereto and capable of contacting and delivering energy to grasped tissue. In an exemplary embodiment, the cutting element 24 is slidably and retractably mated to the jaw 20 to allow a portion of the cutting element 24 to pass through and cut and/or coagulate grasped tissue. The device 10 can also include other features, such as a lever 26 and/or retraction knob 30 mated to the handle 12 for allowing a user to control movements of the jaws 18, 20 and the cutting element 24, respectively.

Figure 2:
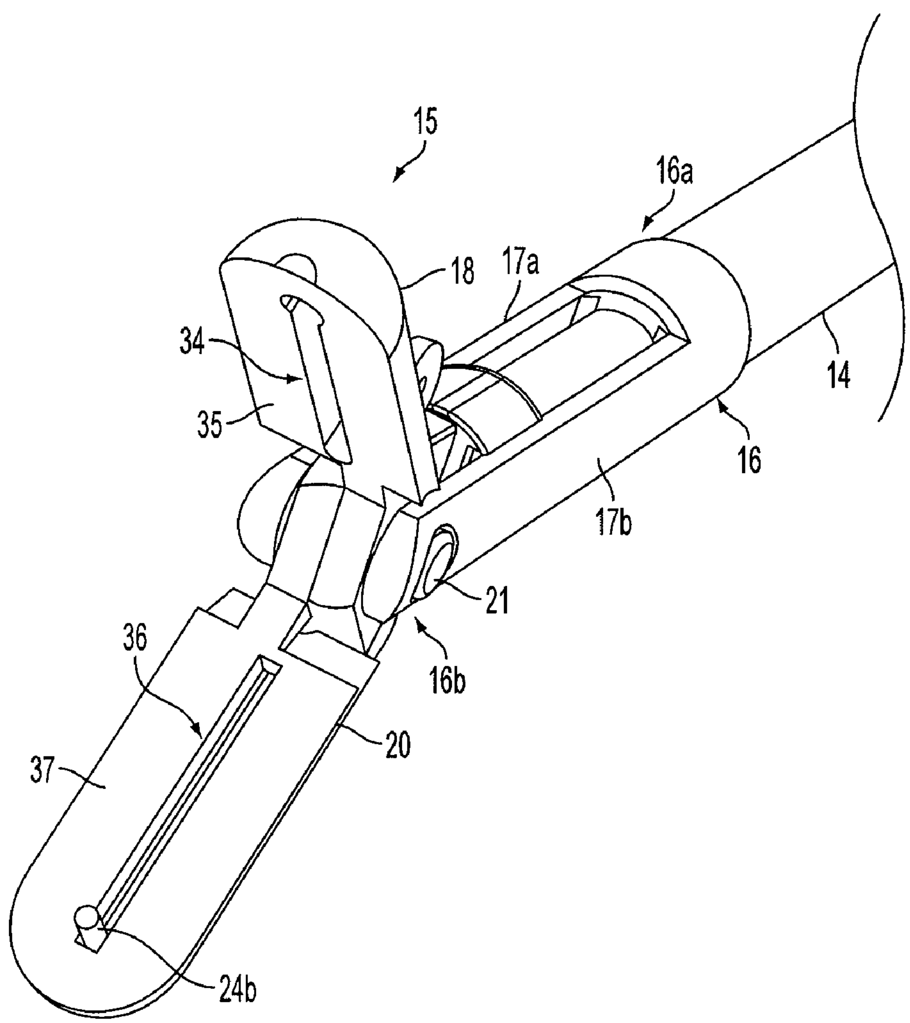
FIG. 2 is a perspective view of a distal portion of the device of the FIG. 1A.
Figure 6:
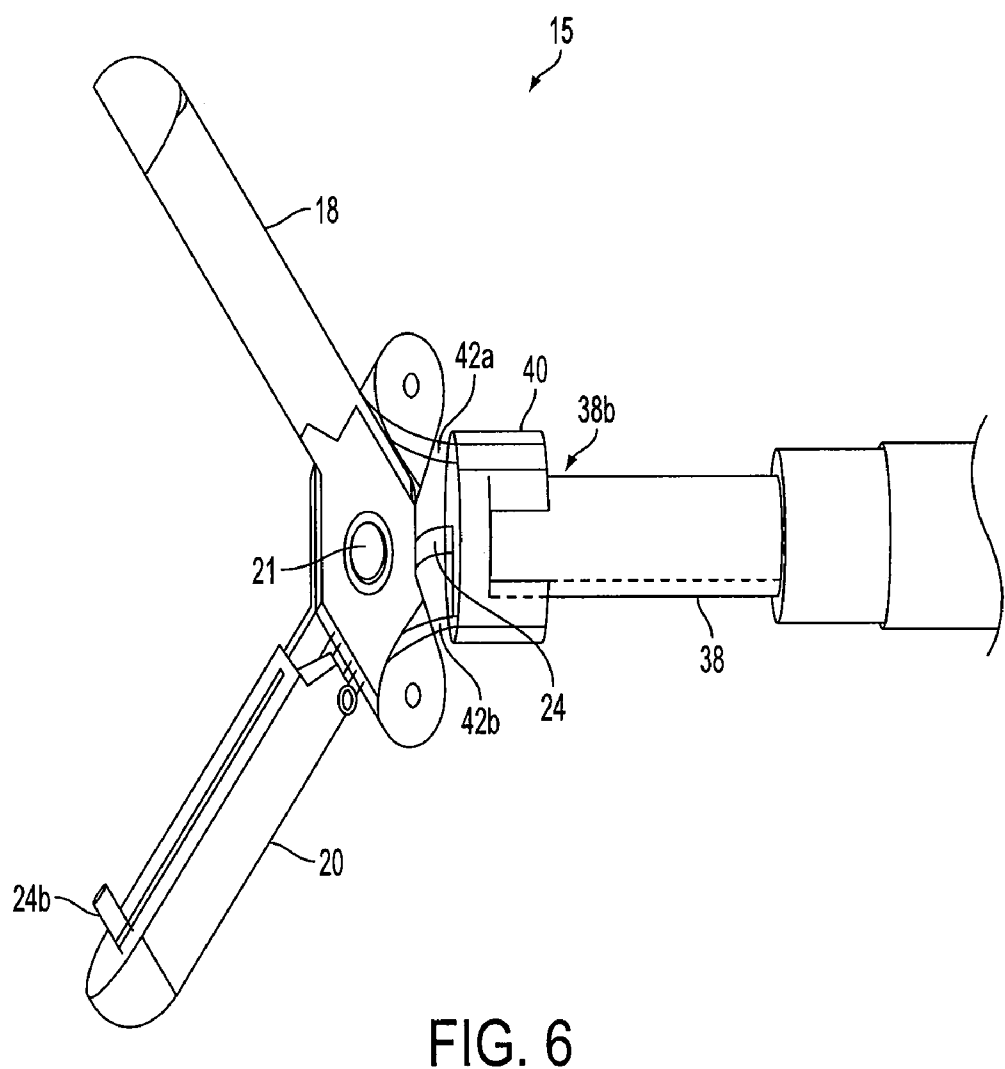
FIG. 6 is a side view of a distal portion of the device of FIG. 1A showing the jaws mated to an internal driver.

The cutting head 15, which is shown in more detail in FIG. 2, can have a variety of configurations, but as indicated above the cutting head 15 preferably includes opposed jaws 18, 20 adapted to engage tissue therebetween. The jaws 18, 20 can be mated such that they are capable of pivoting between an open position and a closed position. As shown in FIGS. 1A-2, a proximal portion of each jaw 18, 20 can be pivotally coupled to a connector 16 by a pivot pin 21. The connector 16 can have a variety of configurations, but it is preferably adapted to couple the jaws 18, 20 to the distal end 14*b* of the elongate shaft 14. The shaft 14 can, however, be configured to mate directly to the jaws 18, 20. As shown in FIG. 2, the connector 16 has a generally cylindrical shape and includes proximal and distal ends 16*a*, 16*b*. The proximal end 16*a* of the connector 16 is fixedly mated to the distal end 14*b* of the shaft 14. The connector 16 can, however, be rotatably mated to the shaft 14 thereby allowing the jaws 18, 20 to rotate about the longitudinal axis of the shaft 14. The distal end 16*b* of the connector 16 can include opposed arms 17*a*, 17*b* that receive the pivot pin 21 for mating the jaws 18, 20 to the connector 16. The opposed arms 17*a*, 17*b* can also receive a proximal portion of each jaw 18, 20 therebetween to allow the jaws 18, 20 to move relative to one another. As will be explained in more detail below with respect to FIG. 6, a proximal end of each jaw 18, 20 can be mated to an actuator for effecting pivotal movement of the jaws 18, 20 between the open and closed positions.

The particular shape of each jaw 18, 20 can also vary, but in an exemplary embodiment each jaw 18, 20 has a generally elongate shape. However, those skilled in the art will appreciate that jaws of various shapes are within the spirit and scope of the present invention. In the embodiment shown in FIG. 2, the top jaw 18 can include a first tissue engaging surface 35 and the bottom jaw 20 can include a second opposed tissue engaging surface 37. While the surfaces 35, 37 can have various configurations, in one exemplary embodiment the surfaces 35, 37 are substantially flat in order to provide an optimal surface area for contacting tissue. The surfaces 35, 37 can, however, include features to facilitate grasping of tissue, such as ridges, teeth, or other surface features, and/or various chemical treatments. As further shown, each jaw 18, 20 can include a recess 34, 36 formed therein and extending from a proximal end to a distal end of each jaw 18, 20. As will be discussed in detail below, at least one of the recesses, e.g., recess 36, can be adapted to allow a portion of the cutting element 24 to protrude from the jaw and slide along the length of the recess thereby cutting tissue grasped between the jaws 18, 20. The other recess, e.g., recess 34, can be adapted to receive the protruding portion of the cutting element 24.

The jaws 18, 20 can also formed from various materials. In an exemplary embodiment, the jaws 18, 20 are formed from a non-conductive material, such as a polymer or mixture of polymers. The jaws 18, 20 can, however, include conductive portions, such as a metal surface formed or disposed on a portion of the tissue-engaging surface 35, 37.

Figure 3:
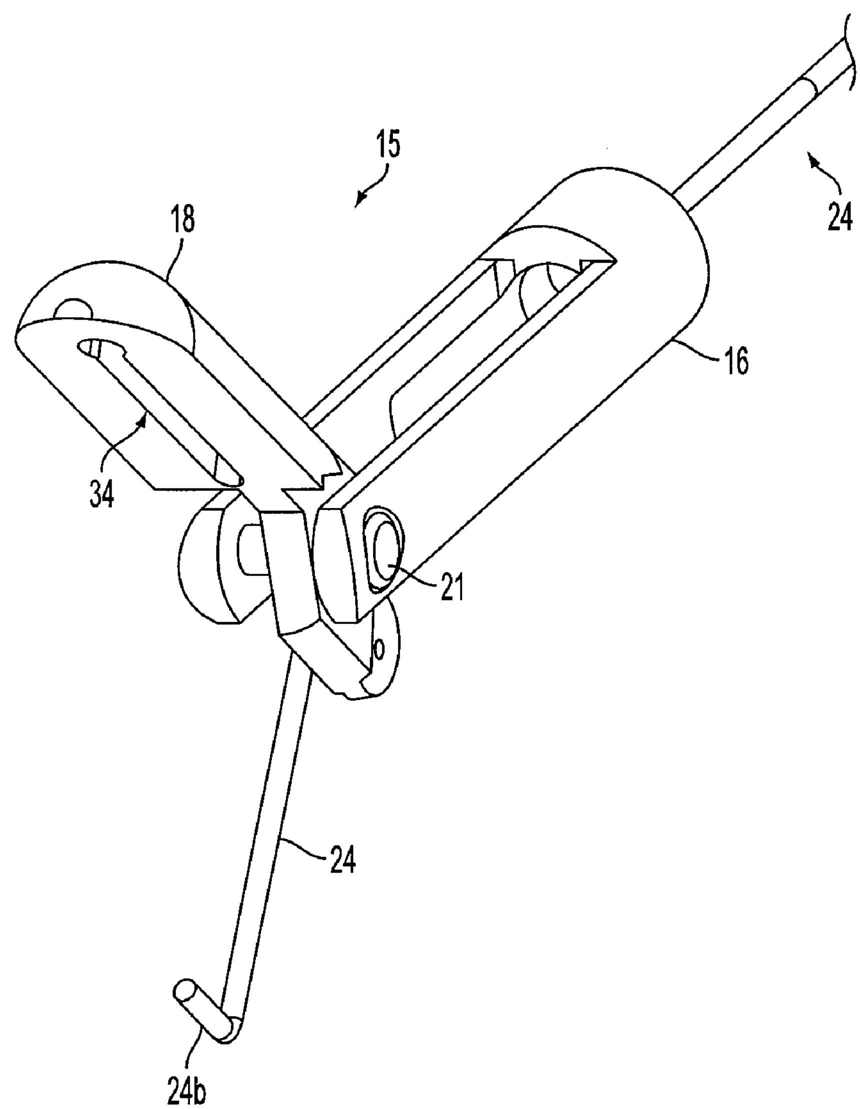
FIG. 3 is a perspective view of the distal portion of the device of FIG. 2, showing certain components removed in order to illustrate a cutting element of the device.

As previously indicated, at least one of the jaws 18, 20 can include at least one cutting element 24 mated thereto. Generally, the cutting element 24 can be any element that is capable of delivering energy to tissue engaged between the jaws. In an exemplary embodiment, as shown in FIG. 3, the cutting element 24 is in the form of a generally elongate wire or needle having a proximal end 24*a* that is adapted to couple to an energy source, and a distal end 24*b* that is adapted to extend through the recess 36 in the jaw 20 to cut and/or coagulate tissue grasped between the jaws 18, 20. The cutting element 24 can, however, be formed from various segmented components that are electrically and mechanically coupled to one another. At least the distal end 24*b* of the cutting element 24 can form an active portion of the cutting element 24 that serves as an electrode capable of delivering energy to tissue. In the illustrated embodiment, the entire cutting element 24 is active to allow energy to pass therethrough. In other embodiments, certain portions, such as the distal end 24*b*, can form an active electrode, while the remainder of the cutting element 24 can be inactive. In addition, various portions of the cutting element 24 can be treated with a non-conductive material, such as a non-conductive coating, to prevent energy dissipation as energy propagates towards the distal end 24*b*.

As indicated above, in an exemplary embodiment the distal end 24*b* of the cutting element 24 protrudes out of the recess 36 in the bottom jaw 20 and is adapted to extend through tissue grasped between the jaws 18, 20. As shown in FIGS. 2 and 3, the distal end 24*b* of the cutting element 24 extends at an angle relative to a longitudinal axis of the jaw 24 and of the remainder of the cutting element 24 to allow the distal end 24*b* to protrude out of the recess 36 in the bottom jaw 20. While the particular angle can vary, in an exemplary embodiment the distal end 24*b* extends substantially perpendicular to the remainder of the cutting element 24 and to the longitudinal axis of the jaw 20. The remainder of the cutting element 24 can extend through a lumen formed in the bottom jaw 24, and through the connecting element 16 and the shaft 14 and into the handle 12.

The cutting element 24 can also be formed from a variety of conductive materials capable of carrying, propagating, and delivering monopolar energy from an energy source to the distal end 24*b* and ultimately to tissue. In addition, the cutting element 24 can be formed from a resilient material that allows the cutting element 24 to flex in response to opening and closing of the jaws 18, 20.

Figure 4A:
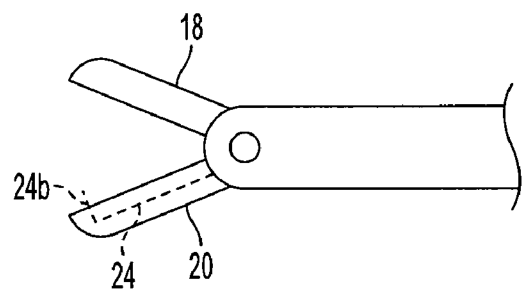
FIG. 4A is a side view of the jaws of the device of FIG. 1A in an open position and having a cutting element in an extended position.
Figure 4B:
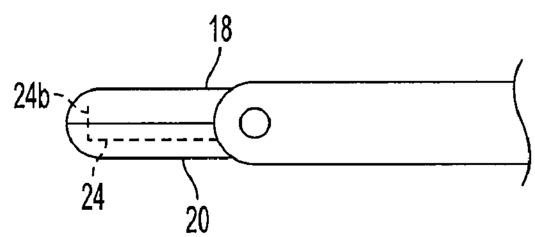
FIG. 4B is a side view of the jaws of FIG. 4A in a closed position and the cutting element in the extended position.
Figure 4C:
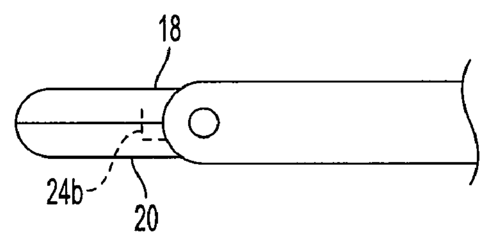
FIG. 4C is a side view of the jaws of FIG. 4A in the closed position and the cutting element in a retracted position.

FIGS. 4A-4C illustrate the relative movements of the jaws 18, 20 and cutting element 24. FIG. 4A illustrates a first stage wherein the jaws 18, 20 are in an open position and the cutting element 24 is in an extended position such that the distal end 24*b* of the cutting element 24 is located adjacent to the distal end of the jaw 20. In this position, the jaws 18, 20 can be placed adjacent to tissue to be grasped between the jaws. FIG. 4B illustrates a second stage wherein the jaws 18, 20 have moved from the open position of FIG. 4A to a closed position in which the jaws 18, 20 are effective to grasp tissue therebetween. At this stage, the cutting element 24 remains in the extended position. FIG. 4C illustrates a third stage wherein the jaws 18, 20 remain in a closed position while the cutting element 24 is moved from the extended position to a retracted position. In particular, the cutting element 24 slides proximally through the recess in the jaw 20, thereby passing through tissue engaged between the jaws 18, 20. Energy can be simultaneously delivered to the cutting element 24 during retraction to cut and/or coagulate the tissue. In the final retracted position, shown in FIG. 4C, the distal end 24*b* of the cutting element 24 will be located adjacent to the proximal ends of the jaws 18, 20. After the first, second, and third stages have been performed, the jaws 18, 20 and/or cutting element 24 can be returned to their original positions to repeat the procedure if necessary or to treat a second tissue.

Various techniques can be used to move the jaws 18, 20 between the open and closed positions, to move the cutting element 24 between the extended and retracted positions, and to deliver energy to the cutting element 24. In an exemplary embodiment, the device includes a handle 12 having a lever 26 for actuating, i.e., opening and closing, the jaws 18, 20, and a retraction knob 30 for sliding the cutting element 24 and simultaneously activating energy delivery to the cutting element 24. The particular shape and configuration of the handle 12 can vary, but in general it is preferably adapted to be grasped by a user to allow the user to manipulate the device 10. The handle 12 can be formed from a single housing or it can include two housing halves that are coupled together. The handle 12 can also include other features not shown, such as a rotation knob for rotating the cutting head 15 relative to the elongate shaft 14, or for rotating the elongate shaft 14 relative to the handle 12.

Figure 5A:
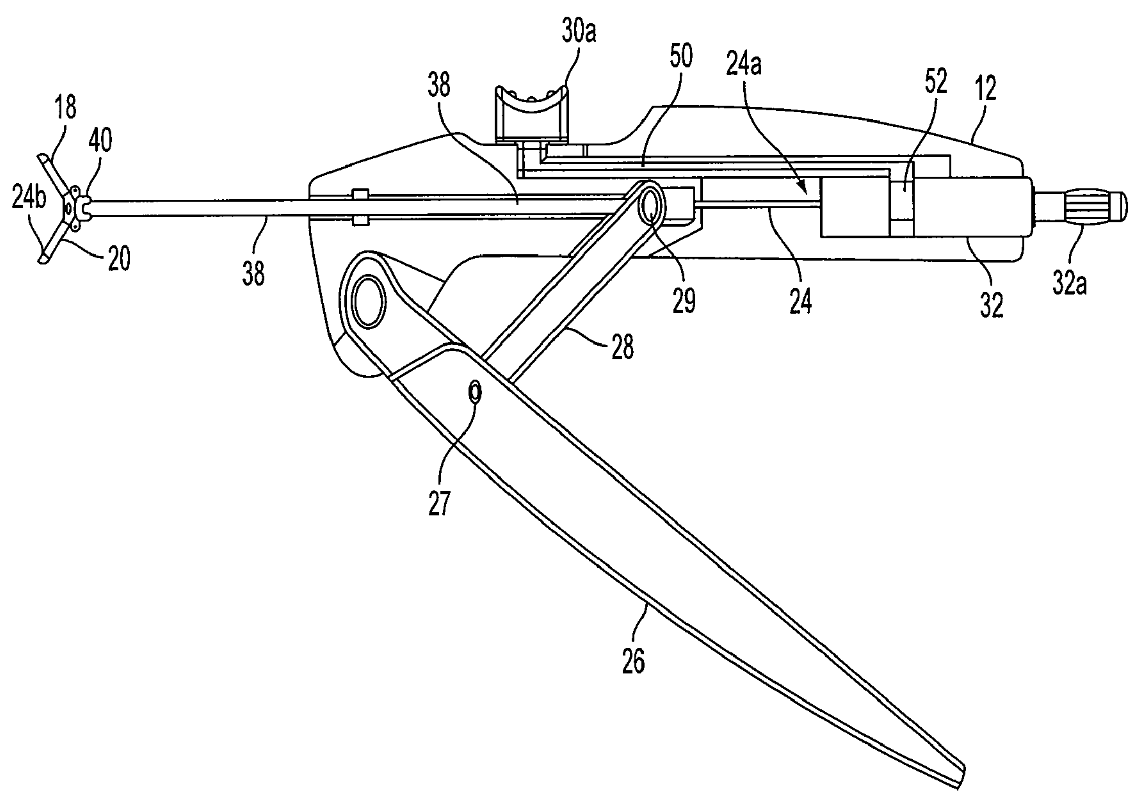
FIG. 5A is a side view of the device of FIG. 1A with a portion of the handle housing removed to show the internal components of the device.

The lever 26 used to open and close the jaws 18, 20 can have a variety of configurations, and various levers, knobs, or other mechanisms known in the art can be used to actuate the jaws 18, 20. In the illustrated embodiment, the lever 26 is in the form of a trigger that is pivotally coupled to the handle 12 and that is movable between an open position, as shown in FIG. 5A, and a closed position in which the lever 26 is positioned adjacent to and/or in contact with the handle 12. In an exemplary embodiment, the lever 26 is biased to the open position, such that the jaws 18, 20 are likewise biased to the open position. While not shown, a spring or other techniques known in the art can be used to bias the lever 26 to the open position. As further shown in FIGS. 5A and 5B, the lever 36 can include extension arm 28 having a first end 27 that is pivotally coupled to the lever 26, and a second end 29 that is coupled to a proximal end of an actuator 38. The actuator 38 can extend through the handle 12 and through the elongate shaft (not shown in FIGS. 5A and 5B), and a distal end 38*b* of the actuator 38 can be mated to a pusher 40, shown in FIG. 6. The pusher 40 can in turn be coupled to first and second pull wires 42*a*, 42*b* that mate to the top and bottom jaws 18, 20, respectively. As a result, when the lever 26 is moved toward the handle 12, the extension arm 28 will move the actuator 38 proximally, thereby pulling the pusher 40 proximally. The pusher 40 will thus pull the pull wires 42*a*, 42*b* proximally to pull the proximal ends of the jaws 18, 20 toward one another causing the jaws 18, 20 to pivot about the pivot pin 21 to the closed position.

Figure 5B:
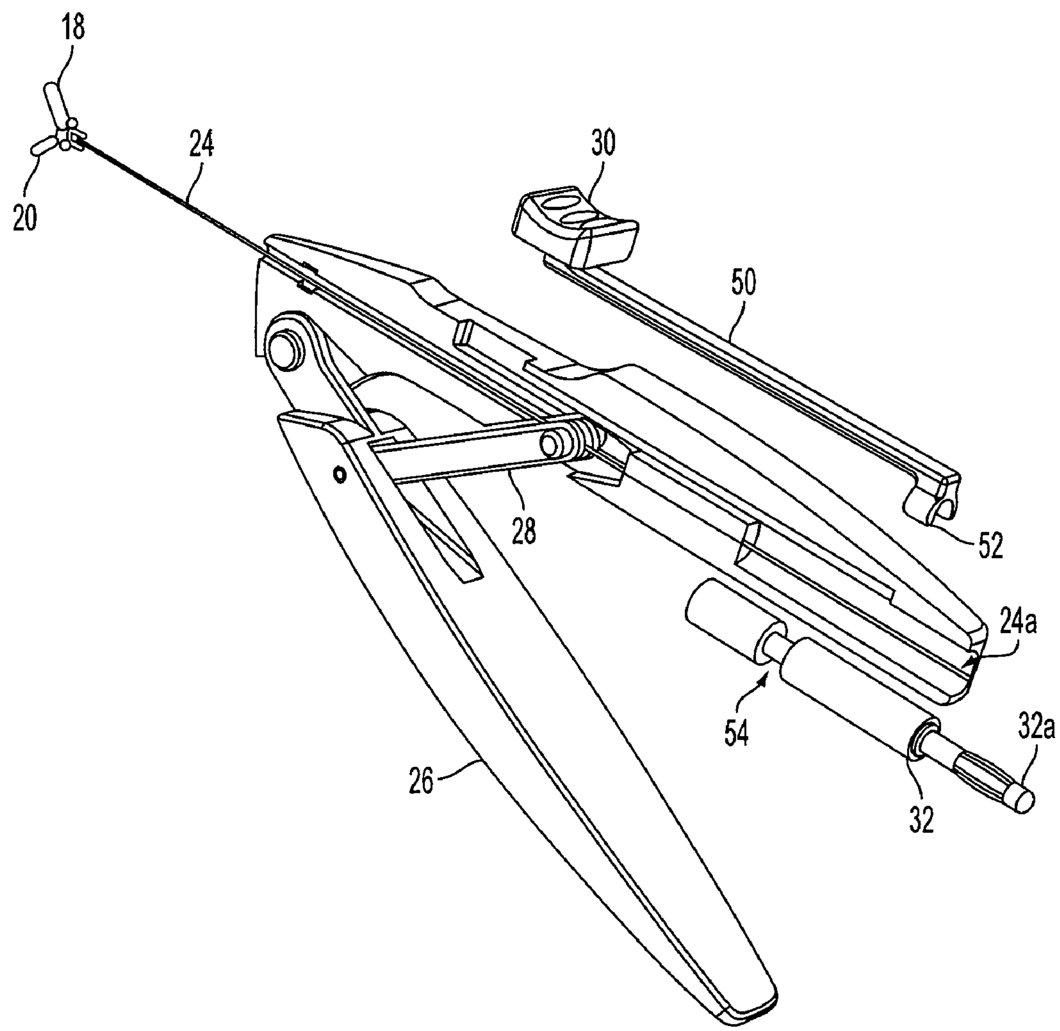
FIG. 5B is a partially exploded view of the device of FIG. 5A.

The retraction knob 30 for sliding the cutting element 24 and simultaneously activating energy delivery to the cutting element 24 can also have a variety of configurations. In the embodiment shown in FIGS. 5A and 5B, the retraction knob 30 is slidably coupled to the handle 12, and includes an extension arm 50 that extends from the knob 30 and through the handle 12 wherein it mates to an adaptor 32. While various techniques can be used to mate the extension arm 50 to the adaptor 32, in the illustrated embodiment the extension arm 50 includes a clip 52 formed on a terminal end thereof that engages a cut-out or groove 54 formed in the adaptor 32. The adaptor 32 can also be coupled to the proximal end 24*a* of the cutting element 24. As a result, when the retraction knob 30 is moved proximally along the handle 12, the extension arm 50 moves the adaptor 32 proximally, thereby pulling the cutting element 24 proximally to move the distal end 24*b* of the cutting element 24 from the extended position to the retracted position. The adaptor 32 can also be adapted to couple to an energy source for delivering energy to the cutting element 24. As shown in FIGS. 5A and 5B, the adaptor 32 includes a plug 32*a* formed thereon and extending proximally from the handle 12 for mating to an energy delivery source, such as an electrosurgical generator. Those skilled in the art will recognize that various electrical adaptors are within the spirit and scope of the present invention. In an exemplary embodiment, the adaptor 32 is a banana plug. An operator can press a conventional foot switch (not shown) coupled to the electrosurgical generator for supplying the energy to the device 10. An example of an electrosurgical energy generator is a unitary mono-polar-bipolar RF generator, such as the Valleylab "FORCE 2" RF Generator manufactured by Valleylab, a division of Tyco Healthcare Group LP, 5920 Longbow Drive, Boulder, Colo., 80301-2199, U.S.A.

Exemplary methods for cutting tissue using monopolar energy are also provided. In an exemplary embodiment, a monopolar resection device, such as device 10, is introduced into the body and the cutting head 15 is positioned adjacent to tissue to be cut and/or coagulated. While the device 10 can be introduced using various surgical methods, including both open and minimally invasive surgical techniques, in an exemplary embodiment the shaft 14 of the device 10 is passed through an endoscope that is disposed through a body lumen, such as the esophagus or the colon. The cutting head 15 of the device 10 is extended distally beyond a distal end of the endoscope such that the cutting head 15 is within the field of view of the endoscope. In certain exemplary embodiments, a Natural Orifice Transluminal Endoscopic Surgery ("NOTES") procedure is used. NOTES is a procedure that allows for access through a body lumen, such as the colon, to organs located in the abdominal cavity. A flexible endoscope is initially inserted through one of the natural orifices, i.e., the stomach (via esophagus), colon, urethra, and vagina, and then the endoscope is passed through an incision and into the abdominal cavity.

Once the cutting head 15 is positioned adjacent to tissue to be treated, the jaws 18, 20 can be used to grasp tissue. In particular, the lever 26 on the handle 12 can be moved toward the handle 12 to pull the actuator 38 proximally and thereby pivot the jaws 18, 20 to the closed position. Once tissue is grasped between the jaws 18, 20, the energy source can be activated to deliver energy to the cutting element 24. This can be achieved by manually activating the energy source, or alternatively the device can be configured such that energy delivery will be automatically activated when the retraction knob 30 is in a predetermined position, e.g., moved proximally by a certain distance. As energy is delivered, the retraction knob 30 can be moved proximally along the handle 12 to pull the cutting element 24 proximally. As a result, the distal end 24*b* of the cutting element 24 will pass through tissue grasped between the jaws 18, 20. Energy delivered to the cutting element 24 will cause the distal end 24*b* of the cutting element 24 to cut and/or coagulate the tissue. Since the cutting element 24 is relatively small, i.e., in the form of a needle or wire, energy delivery will be localized to cut and/or coagulate the grasped tissue without causing damage to adjacent tissue. A person skilled in the art will appreciate that the particular amount of energy delivered to the cutting element 24 can be optimized to obtain the desired result.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue grasping device, comprising:

an elongate shaft having proximal and distal ends;

first and second jaws, each pivotally coupled to the distal end of the elongate shaft and adapted to engage tissue therebetween; and a monopolar cutting element comprising an elongate needle, the monopolar cutting element being:

(a) slidably mated to at least one of the first and second jaws, (b) flexible such that it flexes when the first and second jaws move between open and closed positions, (c) slidably movable between an extended position in which the cutting element is positioned adjacent to a distal end of the first and second jaws, and a retracted position in which the cutting element is positioned adjacent to a proximal end of the first and second jaws, and (d) adapted to couple to an energy source for delivering energy to the monopolar cutting element.

2. The device of claim 1, wherein the first and second jaws have a longitudinal axis, and wherein a distal end of the elongate needle extends substantially transverse to the longitudinal axis.

3. The device of claim 2, wherein a distal end of the elongate needle extends substantially perpendicular to the longitudinal axis of the first and second jaws.

4. The device of claim 1, further comprising a handle mated to the proximal end of the elongate shaft and having an actuator located thereon for moving the first and second jaws between an open position in which the first and second jaws are spaced a distance apart from one another for receiving tissue therebetween, and a closed position in which the jaws are positioned adjacent to one another and adapted to engage tissue therebetween.

5. The device of claim 4, further comprises a retraction knob mated to the handle for moving the cutting element from the extended position to the retracted position.

6. The device of claim 1, wherein a portion of the cutting element extends through an inner lumen of the shaft and includes a proximal end that is adapted to couple to an energy source.

7. The device of claim 1, wherein the elongate shaft is flexible such that the elongate shaft is adapted to be inserted through a tortuous body lumen.

8. A method for processing the device of claim 1 for surgery, comprising:

a) obtaining the device of claim 1;

b) sterilizing the device; and c) storing the device in a sterile container.

9. A tissue grasping device, comprising:

a handle having a flexible elongate shaft extending distally therefrom;

opposed jaws coupled to a distal end of the flexible elongate shaft and adapted to engage tissue therebetween, wherein each opposed jaw is pivotally coupled to the distal end of the elongate shaft; and at least one monopolar cutting element comprising an elongate needle, the monopolar cutting element being:

(a) slidably mated to at least one of the opposed jaws and adapted to slide relative to a longitudinal axis of the opposed jaws to cut tissue engaged between the opposed jaws, and (b) flexible such that the monopolar cutting element flexes when the opposed jaws move between open and closed positions.

10. The device of claim 9 further comprising a retraction knob coupled to the handle and adapted to slidably move at least one cutting element relative to the opposed jaws.

11. The device of claim 9, wherein the at least one cutting element includes a proximal portion extending through the elongate shaft and a distal portion protruding from at least one of the opposed jaws.

12. The device of claim 11, wherein the distal portion extends substantially perpendicular to a longitudinal axis of the first and second jaws.

13. The device of claim 9, further comprising an actuator operatively associated with the first and second jaws and adapted to move the first and second jaws between an open position in which the first and second jaws are spaced a distance apart from one another for receiving tissue therebetween, and a closed position in which the jaws are positioned adjacent one another and adapted to engage tissue therebetween.

14. A method for cutting tissue, comprising:

positioning tissue to be cut between opposed jaws pivotally coupled to a distal end of an elongate shaft of a tissue grasping device;

moving the opposed jaws to a closed position to engage the tissue disposed therebetween, wherein moving the opposed jaws comprises pivoting both jaws to the closed position;

activating a monopolar energy source to deliver energy to a cutting element coupled to the opposed jaws wherein the cutting element flexes when the opposed jaws are moved to the closed position; and slidably retracting the cutting element relative to the opposed jaws to cut the tissue.

15. The method of claim 14, wherein slidably retracting the cutting element comprises actuating a force to a retraction knob that is operatively associated with the cutting element to slide the cutting element from an extended position in which the cutting element is disposed within a distal end of the opposed jaws, to a retracted position in which the cutting element is disposed within the proximal end of the opposed jaws.

16. The method of claim 14, wherein moving the opposed jaws to a closed position comprises actuating a trigger formed on a handle to move the opposed jaws from an open position in which the opposed jaws are spaced a distance apart from one another, to the closed position.

17. The method of claim 14, further comprising, prior to positioning tissue, inserting a flexible elongate shaft of the tissue grasping device through a tortuous body lumen to position the opposed jaws located on a distal end of the flexible elongate shaft adjacent to the tissue to be cut.

18. The method of claim 14, further comprising, prior to positioning tissue, delivering the opposed jaws of the tissue grasping device to an abdominal cavity via a natural orifice.

19. The method of claim 14, further comprising sterilizing the tissue grasping device after at least one use.

* * * * *